US00PP36359P2

(12) United States Plant Patent
Horvath

(10) Patent No.: US PP36,359 P2
(45) Date of Patent: Dec. 31, 2024

(54) ***SCHIZACHYRIUM SCOPARIUM* PLANT NAMED 'Sandhill'**

(50) Latin Name: *Schizachyrium scoparium*
Varietal Denomination: Sandhill

(71) Applicant: Brent Horvath, Hebron, IL (US)

(72) Inventor: Brent Horvath, Hebron, IL (US)

( * ) Notice: Subject to any disclaimer, the term of this patent is extended or adjusted under 35 U.S.C. 154(b) by 0 days.

(21) Appl. No.: 18/445,914

(22) Filed: Mar. 26, 2024

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384
See application file for complete search history.

(56) References Cited

U.S. PATENT DOCUMENTS

PP25,202 P2 * 12/2014 Castorani ..... A01H 6/46
Plt./384

* cited by examiner

*Primary Examiner* — Karen M Redden

(57) ABSTRACT

A new, distinct *Schizachyrium scoparium* plant as illustrated and described, characterized by a height of 120 cm, extra wide gray-green colored foliage.

2 Drawing Sheets

Figure 1:
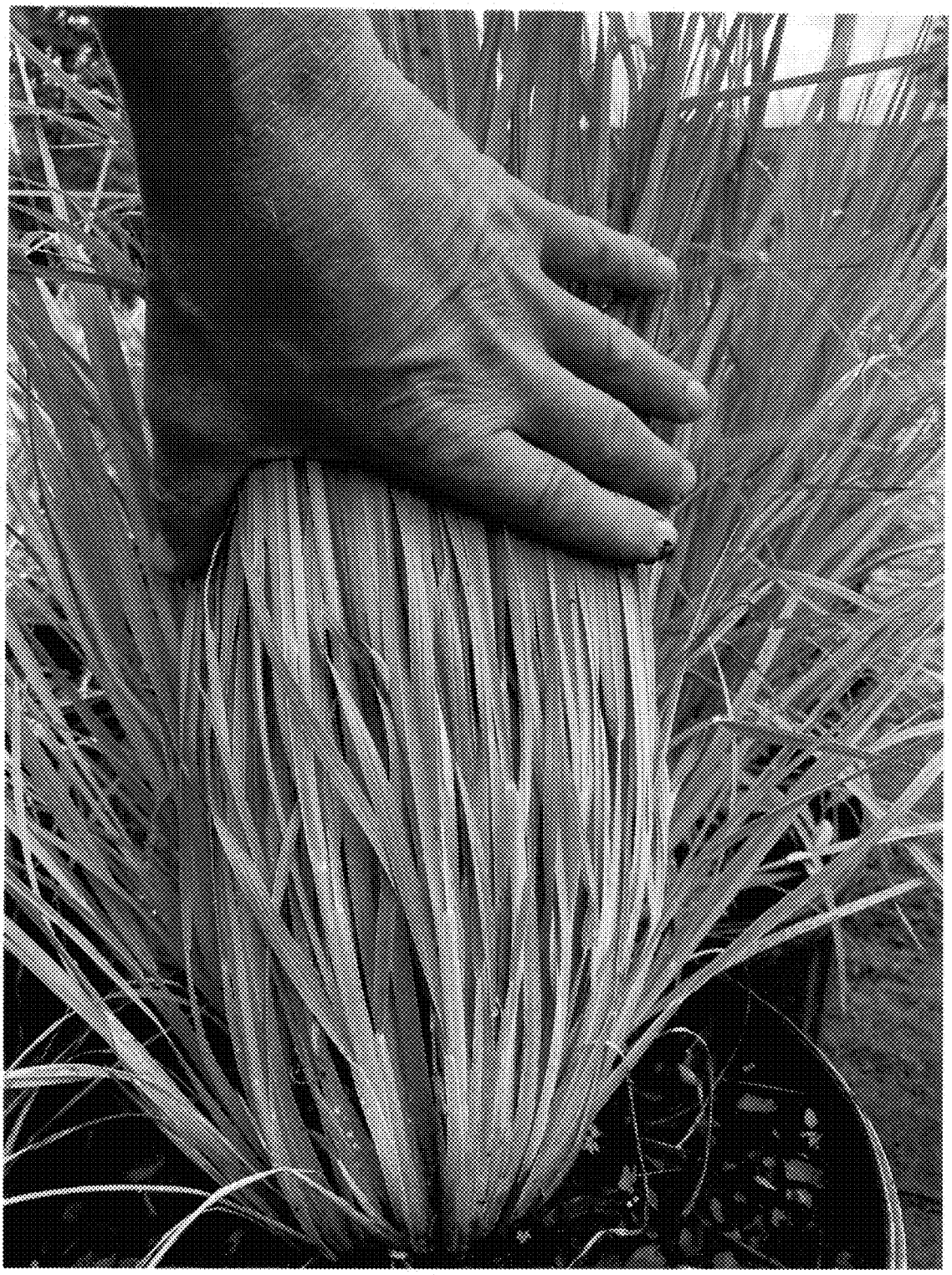

Latin name: *Schizachyrium scoparium.*
Cultivar name: 'Sandhill'.

BACKGROUND OF THE INVENTION

The present invention relates to a new form of *Schizachyrium scoparium* plant named 'Sandhill'. 'Sandhill' is a seedling selection of *Schizachyrium scoparium*, characterized by a height of 120 cm, extra wide gray-green colored foliage. The new plant was grown as a seedling of an unnamed selection of *Schizachyrium scoparium*, by the inventor at a wholesale perennial nursery in Hebron, IL USA in 2019. The selection of this plant was due to its height of 120 cm, and extra wide gray-green colored foliage. Asexual, vegetative division propagation has been the only means of reproduction. Initial vegetative propagation has taken place at Hebron, IL since 2020. In 2022 we planted 200 plants. To date these plants have remained uniform in height, and foliage color. The new *Schizachyrium scoparium* has shown to be stable and identical in reproduction to the parent after making over 2000 vegetative divisions from 2020 to 2023. No plants of *Schizachyrium scoparium* plant named 'Sandhill' have been sold in this country, or anywhere in the world, prior to the filing of this application, nor has any disclosure of the new plant been made prior to the filing of this application with the exception of that which was disclosed by the inventor and his nursery in Hebron, IL US and his licensees within one year of the filing of this application and was either derived directly or indirectly from the inventor. Actual first date of sale was Apr. 18, 2023.

SUMMARY OF THE INVENTION

In the following description, color references are made to The Royal Horticultural Society Colour Chart (copyright 2001). The new *Schizachyrium scoparium* plant named 'Sandhill' has shown the characteristics of a height of 120 cm, and extra wide gray-green colored foliage to be unique and stable. For purpose of the comparison the new plant will be referred to as 'Sandhill'.

Plants of 'Sandhill' can be compared to plants of *Schizachyrium scoparium* 'MinnblueA' U.S. Plant Pat. No. 17,310. 1. 'Sandhill' has wider gray-green foliage measuring up to 9 mm wide compared to the foliage width of *Schizachyrium scoparium* 'MinnblueA' which has an average width of 4 mm. 2. 'Sandhill' has spring foliage color of RHS 137 B coloring to 191 A in summer compared to *Schizachyrium scoparium* 'MinnblueA' which has summer foliage color of 122 C and 122 D.

Plants of 'Sandhill' can be also be compared to plants of *Schizachyrium scoparium* 'Standing Ovation', U.S. Plant Pat. No. 25,202. 1. 'Sandhill' has wider gray-green foliage measuring up to 9 mm wide compared to the foliage width of *Schizachyrium scoparium* 'Standing Ovation' which has an average width of 6 mm. 2. 'Sandhill' has spring foliage color of RHS 137 B coloring to 191 A in summer compared to *Schizachyrium scoparium* 'Standing Ovation' which has foliage color that is, RHS 189 A in spring and summer.

Plants of 'Sandhill' can be also be compared to plants of *Schizachyrium scoparium* 'Prairie Blues' (not patented). 1. 'Sandhill' has a height of 120 cm compared to the height of *Schizachyrium scoparium* 'Prairie Blues' which has an average height of 80-90 cm. 2. 'Sandhill' has wider gray-green foliage measuring up to 9 mm wide compared to the foliage width of *Schizachyrium scoparium* 'Prairie Blues' which has an average width of 3 mm. 3. 'Sandhill' has a foliage color of RHS 137 B coloring to 191 A in summer compared to *Schizachyrium scoparium* 'Prairie Blues', which has foliage color close to 190 B.

DESCRIPTION OF PHOTOGRAPHS

FIG. 1. Shows a 2 year old plant in July in Hebron, IL USA.

Figure 2:
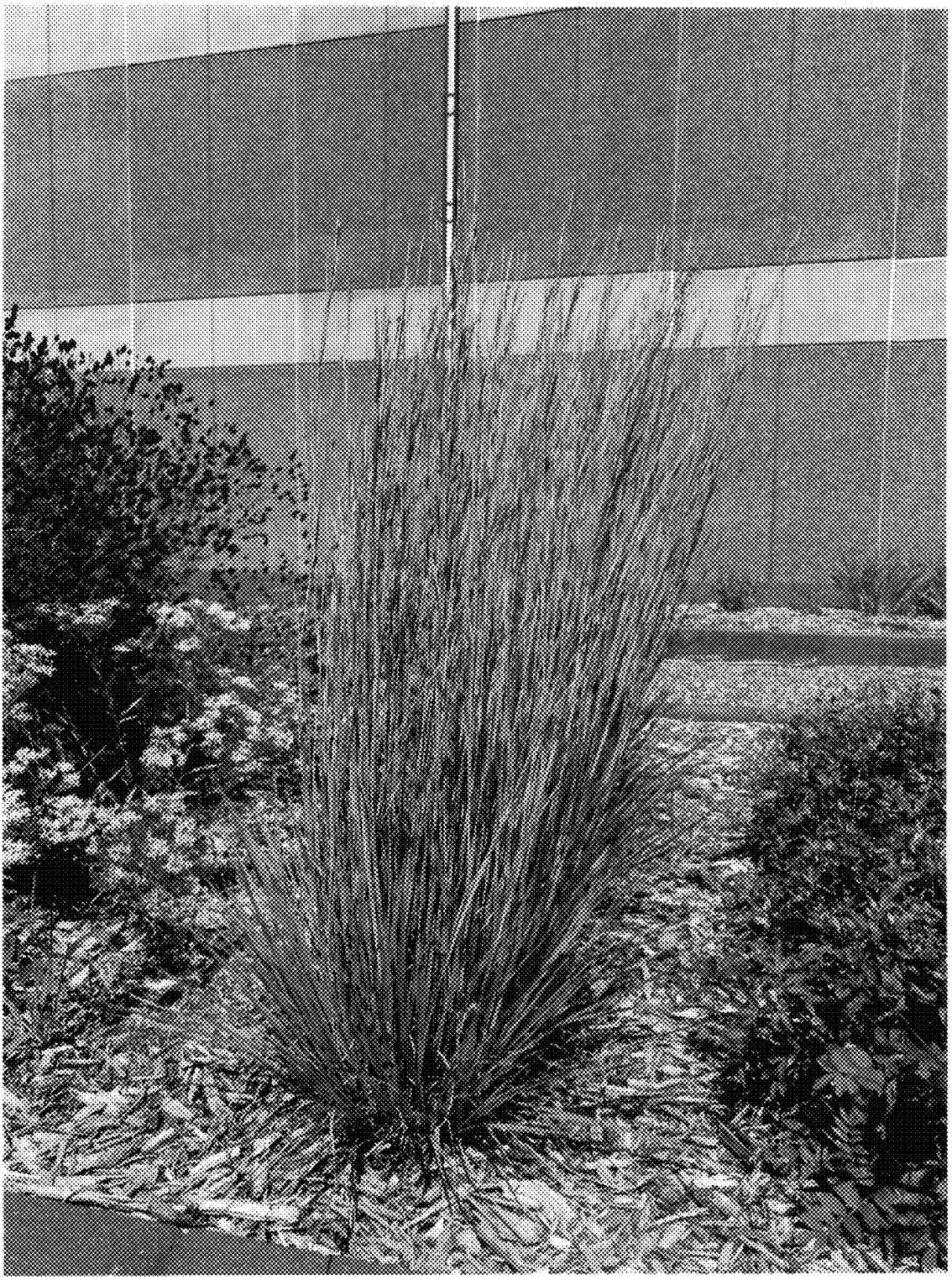

FIG. 2. Shows a 2 year old plant in September in Cottage Grove, MN USA.

DETAILED BOTANICAL DESCRIPTION

In the following description, color references are made to The Royal Horticultural Society Colour Chart 2001. The plant herein described is an established 2 year old plant growing in a garden, grown in full sun and irrigated in Hebron, IL USA. Measurements and numerical values represent averages of typical plants.

Botanical classification: *Schizachyrium scoparium* plant named 'Sandhill'

Parentage: Female: An open pollinated *Schizachyrium scoparium* selection. Male: an unnamed and unknown *Schizachyrium scoparium* selection Propagation: Vegetative division.

Plant description: Overall habit of the new *Schizachyrium scoparium* is clumping with upright culms topped by silvered colored flowers beginning in September. Vigor is moderate.

*Plant height.*—120 cm.

*Plant width.*—70 cm.

Foliage and stems:

*Foliage description.*—Glabrous, flat blade, sheathed from node of attachment to ligule, linear.

*Type.*—Deciduous, grass growing in culms.

*Shape.*—Linear.

*Sheath.*—15 mm wide, 11 cm long, surface-glabrous.

*Ligules.*—Less than 1 mm long and less than 1 mm wide.

*Number of blades.*—Typically 6 blades per stem.

*Blade size.*—10 mm wide, up to 54 cm long, average 45 cm without the sheath.

*Adaxial leaf description.*—Leaf color emerging is 137 B coloring up to 191 A in summer and has fall color close to 61 B.

*Abaxial leaf description.*—Leaf color emerging is N138 B coloring up to 191 B in summer and has fall color close to 61 B.

*Veins.*—Parallel, same color as surrounding leaf on both top and bottom of leaf.

*Culm description.*—Erect, cylindrical, typically with 3 leaves.

*Culm or stem diameter.*—7-8 mm average, but typically 6-7 mm between the nodes and swelling to 7 mm at the base of the internodes.

*Number of culms or stems per clump.*—Over 30.

*Culm color.*—Ranges from 191 B in summer to 61 B in fall.

*Node description.*—Cylindrical.

*Number of nodes per culm.*—Average 6.

*Length of internodes.*—Ranges from 15-20 cm.

Flower inflorescence:

*Inflorescence type.*—Terminal raceme with sessile and pedicillate spikelets.

*Rachis.*—1-2 mm wide and up to 54 cm long, color starts 191 B coloring to 61 B in fall.

*Overall raceme size.*—12 mm wide, 11-17 cm long.

*Rachilla.*—1 mm wide, 9 mm long, color starts 191 B coloring to 61 B in fall.

*Inflorescence color.*—As a whole the color is close to N155 A.

*Spikelet.*—Sessile and pedicellate — Both 11 mm wide 15 mm long, color is close to N155 A.

*Individual floret size.*—1 mm wide, 15 mm long including awn.

*Lower glume.*—1 mm wide, 11 mm long, color starts 191 B with fine hairs less than 1 mm wide and 9-11 mm long, color near N155 A.

*Upper glume.*—1 mm wide, 9 mm long, color starts 137 B coloring to 187 A with fine hairs less than 1 mm wide and 9 mm long, color near N155 A.

*Lemma.*—Outer and inner-both, less than 1 mm, 9 mm long, color starts 137 B coloring up to 187 A.

*Awn size.*—Is less than 1 mm wide and average 13 mm long.

*Pedicels.*—5 to 6 per, 1 mm wide and 15 cm long.

*Flower number.*—Approximately 42 florets per rames, average 120 per spikelet, mature spikelet measuring 9 mm wide, 13 mm long.

*Gynoecium.*—Stigma — 2. Color close to 187 A.

*Androecium.*—Anthers — number 3, color — is 187 A.

*Anther size.*—2-3 mm long by 1 mm wide.

*Fertility.*—Fertile with 3 Anthers and 3 Stamens.

*Blooming habit.*—Terminal raceme on up to 120 cm stems.

*Bloom period and duration.*—Last two weeks of August to the end of September.

*Bloom color.*—187 A.

*Fruit or seeds.*—Color is close to N155 A, size is 1 mm wide, 11 mm long.

*Scent.*—No scent.

*Roots.*—Fibrous, and freely branching.

*Fruit.*—Seed identical to the species.

*Hardiness.*—United States Department of Agriculture Zones 4-9.

*Disease resistance.*—Plants are not susceptible to any major pests or diseases.

I claim:

1. A new, distinct *Schizachyrium scoparium* plant named 'Sandhill', substantially as described and illustrated, herein.

* * * * *